United States Patent [19]
Malen et al.

[11] Patent Number: 5,173,502
[45] Date of Patent: Dec. 22, 1992

[54] SUBSTITUTED TRIFLUOROPROPAN-1-YL-IMIDAZOLE ALPHA 2-RECEPTOR ANAGONISTS

[75] Inventors: Charles Malen, Fresnes; Guillaume de Nanteuil, Suresnes, both of France

[73] Assignee: Adir et Compagnie, Courbevoie, France

[21] Appl. No.: 786,280

[22] Filed: Nov. 1, 1991

[30] Foreign Application Priority Data

Nov. 14, 1990 [FR] France ................... 90 14086

[51] Int. Cl.$^5$ ............... A61K 31/415; A61K 31/44; C07D 233/64; C07D 401/06
[52] U.S. Cl. .................... 514/396; 514/341; 514/397; 514/399; 514/400; 548/343.1; 548/341.5; 548/334.1; 546/278
[58] Field of Search ............... 546/278; 548/336, 342; 514/341, 396, 397, 399, 400

[56] References Cited
U.S. PATENT DOCUMENTS 4,576,958 3/1986 Wexler et al. ................ 548/342

Primary Examiner—Patricia L. Morris
Attorney, Agent, or Firm—Gordon W. Hueschen

[57] ABSTRACT

A compound selected from those of formula (I):

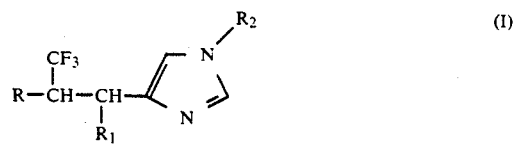

in which
R represents straight-chain or branched lower ($C_1$–$C_6$) alkyl, ($C_3$–$C_8$) cycloalkyl, optionally substituted phenyl, pyridyl or naphthyl, and
$R_1$ and $R_2$, which are the same or different, each represents hydrogen, straight-chain or branched ($C_1$–$C_6$) alkyl, or straight-chain or branched ($C_1$–$C_6$) acyl, an enantiomer, diastereoisomer and epimer, and an addition salt thereof with a pharmaceutically-acceptable acid.

Medicinal product, which is useful as $\alpha_2$-antagonist.

9 Claims, No Drawings

SUBSTITUTED TRIFLUOROPROPAN-1-YL-IMIDAZOLE ALPHA 2-RECEPTOR ANAGONISTS

The present invention relates to new imidazole compounds.

A great number of imidazole compounds have been described in the literature. Some of them interact more specifically with the $\alpha_2$-adrenergic receptors and exhibit sedative properties in the case of agonists, and antidepressant properties in the case of antagonists.

EP 247 764, EP 183 492 and U.S. Pat. No. 4,497,818 patents, for example, describe compounds that are $\alpha_2$-adrenergic antagonists.

The compounds of the present invention differ from those described in the prior art in that the imidazole is substituted at the 4(5) position by an aliphatic chain comprising a trifluoromethyl group.

Furthermore, in addition to the fact that they are new, they have very valuable pharmacological properties.

Indeed, they are effective both on the central nervous system and on the peripheral nervous system through the indirect means of the $\alpha_2$-receptors for which they have a very strong affinity accompanied by a very high selectivity in relation to the $\alpha_1$-adrenergic receptors.

In addition, as a result of their $\alpha_2$-antagonist action, they facilitate the release of noradrenaline from the sympathetic nerve endings and can thus be used in the treatment of disorders associated with a deficiency of available noradrenaline at the post-synaptic adrenergic receptors of the central or peripheral nervous system, such as depression, hypertension, Parkinson's disease, asthma, convulsive states or platelet aggregation.

Finally, as carbohydrate and lipid metabolism is regulated by an inhibiting mechanism at the $\alpha_2$-receptors level, the compounds of the present invention can also be used to treat metabolic disorders, such as diabetes and obesity.

The present invention relates more especially to compounds of formula (I):

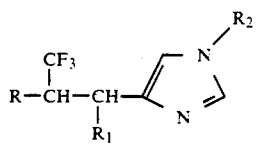

(I)

in which:

R represents a straight-chain or branched lower ($C_1$-$C_6$) alkyl group, a ($C_3$-$C_8$) cycloalkyl group, a phenyl group (optionally substituted by one or more halogen atoms, one or more straight-chain or branched ($C_1$-$C_6$) alkyl groups (themselves optionally substituted by one or more halogen atoms) or one or more straight-chain or branched ($C_1$-$C_6$) alkoxy groups), a pyridyl group or a naphthyl group, and $R_1$ and $R_2$, which are the same or different, each represents a hydrogen atom, a straight-chain or branched ($C_1$-$C_6$) alkyl group, or a straight-chain or branched ($C_1$-$C_6$) acyl group, their enantiomers, diastereoisomers or epimers and also their addition salts with a pharmaceutically acceptable acid.

Among the pharmaceutically acceptable acids there may be mentioned by way of non-limiting example hydrochloric, sulphuric, tartaric, maleic, fumaric, oxalic, methanesulphonic, camphoric acid etc.

The process for the preparation of the compounds of formula (I) is characterised in that an organomagnesium compound of formula (II)

(II)

in which R is as defined hereinbefore and X represents a halogen atom, is subjected to the action of trifluoroacetic acid or the sodium salt thereof to yield a ketone of formula (III) in which R is as defined for formula (I),

(III)

which is reacted in the presence of a base, in accordance with the Horner-Emmons reaction, with the phosphonoacetates of formula (IV)

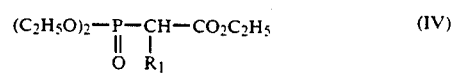

(IV)

in which $R_1$ is as defined in formula (I), to yield the unsaturated esters of formula (V)

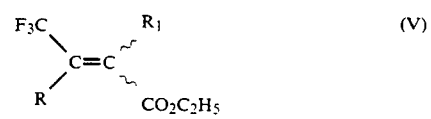

(V)

in which R and $R_1$ are as defined for formula (I), which are subjected to catalytic hydrogenation using, for example, palladium-on-carbon or platinum oxide as catalyst, to yield the esters of formula (VI)

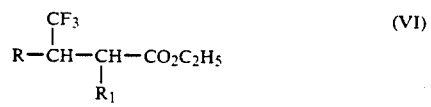

(VI)

in which R and $R_1$ are as defined for formula (I), which are hydrolysed in the presence of aqueous potassium hydroxide or aqueous sodium hydroxide to yield the corresponding acids of formula (VII)

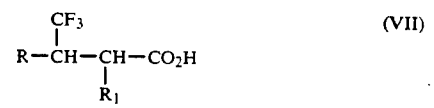

(VII)

in which R and $R_1$ are as defined for formula (I), which are subjected to the action of thionyl chloride to yield the corresponding acid chlorides of formula (VIII) in which R and $R_1$ are as defined for formula (I), which are then treated with excess diazomethane

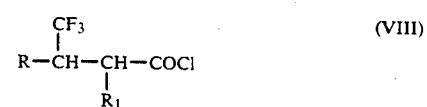

(VIII)

to yield the diazoketones of formula (IX)

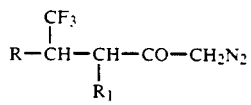

in which R and $R_1$ are as defined for formula (I), which are subjected to the action of gaseous hydrogen chloride to yield the corresponding chloroketones of formula (X)

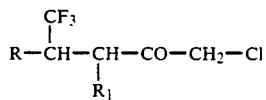

in which R and $R_1$ are as defined for formula (I), which are reacted with formamidine acetate in a solvent having a high boiling point, such as, for example, diethylene glycol, to yield compounds of formula (I) which are purified by conventional purification methods, the isomers of which are optionally separated according to conventional separation methods and which, if desired, are converted into their addition salts with a pharmaceutically acceptable acid.

The compounds of formula (VIII), (IX) and (X) are new and form part of the invention in the same way as the compounds of formula (I), constituting intermediates in the synthesis thereof.

The present invention relates also to pharmaceutical compositions comprising as active ingredient at least one compound of the general formula (I) or an addition salt thereof with a pharmaceutically acceptable acid, alone or in combination with one or more inert non-toxic excipients or carriers.

Among the pharmaceutical compositions according to the invention there shall be mentioned more especially those which are suitable for oral, parenteral, rectal or nasal administration, tablets or dragées, sublingual tablets, sachets, paquets, soft gelatin capsules, glossettes, lozenges, suppositories, creams, ointments, dermal gels, etc.

The dosage used varies in accordance with the age and weight of the patient, the nature and severity of the disorder and the administration route, which may be oral, nasal, rectal, or parenteral. Generally, the unit dosage ranges from 0.1 to 100 mg for a treatment 1 to 3 times per 24 hours.

The following Examples illustrate the invention and do not limit it in any way.

EXAMPLE 1

4-(2-Cyclopentyl-3,3,3-trifluoropropan-1-yl)imidazole hydrochloride

STEP A: Cyclopentyl trifluoromethyl ketone

A suspension of sodium trifluoroacetate (which has been prepared by slowly adding 0.5 mol of trifluoroacetic acid dissolved in THF, at 0° C., to 0.5 mol of sodium hydride suspended in THF) is added to an organomagnesium reagent (which has itself been prepared by adding a solution of 0.5 mol of cyclopentyl bromide in 400 ml of diethyl ether dropwise, while maintaining reflux, to 13.4 g of magnesium turnings placed in 50 ml of anhydrous diethyl ether with an iodine crystal), reflux being maintained for one hour.

The resulting white suspension is refluxed for 2½ hours and maintained at room temperature for one night.

The mixture is then hydrolysed, at 0° C., with 200 ml of 6N hydrochloric acid and 250 ml of water.

The organic phase is subsequently washed with water, then with a 10% bicarbonate solution, and again with water. After drying and evaporating off the solvents, the desired product is obtained by distillation.

Boiling point: 60°-65° C. (150 mm/Hg)
$N_D 21.5°$ C. = 1.377

STEP B: Ethyl 3-cyclopentyl-4,4,4-trifluoro-2-butenoate

A solution of 120 mmols of triethyl phosphonoacetate in 50 ml of dimethoxyethane is added dropwise, at room temperature, to 120 mmols of sodium hydride suspended in 110 ml of dimethoxyethane, while maintaining the temperature below 35° C. That mixture is then stirred at room temperature for 24 hours.

120 mmols of the product obtained in the preceding step are then added dropwise.

After stirring for one hour at room temperature, the mixture is poured onto 1 liter of water. After extraction with ether, washing the ethereal phases with water, drying and evaporating, the desired product is obtained by distillation in vacuo.

Yield: 88%
Boiling point: 105° C. (30 mm/Hg)
$N_D 20.5°$ C. = 1.428

| Elemental microanalysis: | | |
|---|---|---|
| | C % | H % |
| calculated | 55.93 | 6.40 |
| found | 55.69 | 6.37 |

STEP C: Ethyl 3-cyclopentyl-4,4,4-trifluorobutanoate 97 mmols of the product obtained in the preceding step are hydrogenated at room temperature and pressure in 200 ml of methanol in the presence of 1 g of 10% palladium-on-carbon.

After one night, the desired product is obtained in the form of a colourless oil after removing the catalyst by filtration and evaporating off the solvent.

Yield: 98%
$N_D 20.5°$ C. = 1.412

| Elemental microanalysis: | | |
|---|---|---|
| | C % | H % |
| calculated | 55.45 | 7.19 |
| found | 55.21 | 7.01 |

STEP D: 3-Cyclopentyl-4,4,4-trifluorobutanoic acid 170 mmols of 2N aqueous potassium hydroxide solution are added, while cooling with ice, to 86 mmols of the product obtained in the preceding step in 35 ml of methanol.

After one night at room temperature and 2½ hours' reflux, the methanol is evaporated off. The residue is then extracted with ether, and the aqueous phase, acidified with 1N hydrochloric acid, is again extracted with ether.

The desired product is obtained in the form of a colourless oil after drying and evaporation of the ethereal phases.

Yield: 97%

$N_D 22.5°$ C. = 1.419

STEP E: 1-Chloro-4-cyclopentyl-5,5,5-trifluoropentan-2-one 86 mmols of the product obtained in the preceding step together with 430 mmols of thionyl chloride are heated to reflux for 1½ hours.

The corresponding acid chloride is obtained after evaporating off the excess thionyl chloride. It is then added to 170 mmols of diazomethane in 800 ml of diethyl ether. The whole is left for 1 hour at $-5°$ C. and then for 1 hour at $+5°$ C. Dry gaseous hydrogen chloride is then bubbled through that solution for 45 minutes at 0° C. The whole is left for one night at 0° C. After the addition of 100 ml of water, the ethereal phase is extracted, washed with a 10% sodium bicarbonate solution, dried and evaporated.

The desired product is then obtained by distillation in vacuo.

Yield: 78%

Boiling point: 60°–65° C. (0.01 mm/Hg)

|  | Elemental microanalysis: | | |
| --- | --- | --- | --- |
|  | C % | H % | Cl % |
| calculated | 49.50 | 5.82 | 14.61 |
| found | 49.30 | 5.75 | 14.80 |

STEP F: 4-(2-Cyclopentyl-3,3,3-trifluoropropan-1-yl)imidazole hydrochloride 8 mmols of the product obtained in the preceding step are introduced into 50 ml of diethylene glycol with 32 mmols of formamidine acetate. The whole is heated for 50 hours at 135° C.

After cooling, 70 ml of ether and 30 ml of water are added to the above mixture. The aqueous phase is extracted several times with ether. The ethereal phases are combined, dried and then evaporated.

The desired product is obtained in the form of a base after purification by chromatography on silica using as eluant a mixture of heptane, ethanol and ammonium hydroxide (100/5/0.05). The hydrochloride is obtained by means of ethereal hydrogen chloride and is recrystallised from a mixture of ethyl acetate and diisopropyl ether.

Yield: 34%

Boiling point: 99°–100° C.

|  | Elemental microanalysis: | | | |
| --- | --- | --- | --- | --- |
|  | C % | H % | N % | Cl % |
| calculated | 49.17 | 6.00 | 10.43 | 13.19 |
| found | 49.40 | 6.05 | 10.54 | 13.16 |

EXAMPLE 2

4-(2-Phenyl-3,3,3-trifluoropropan-1-yl)-imidazole hydrochloride

The desired product is obtained by proceeding as in Example 1 (Steps B to F), but replacing the cyclopentyl trifluoromethyl ketone in Step B with phenyl trifluoromethyl ketone, and carrying out catalytic hydrogenation in the presence of platinum oxide in step C.

Melting point: 202°–205° C.

|  | Elemental microanalysis: | | | |
| --- | --- | --- | --- | --- |
|  | C % | H % | N % | Cl % |
| calculated | 52.09 | 4.37 | 10.12 | 12.81 |
| found | 52.13 | 4.45 | 10.12 | 12.69 |

EXAMPLE 3

4-(2-Cyclohexyl-3,3,3-trifluoropropan-1-yl)-imidazole hydrochloride

The desired product is obtained by proceeding as in Example 1 but replacing the cyclopentyl bromide in Step A with cyclohexyl bromide.

Melting point: 145°–150° C.

|  | Elemental microanalysis: | | | |
| --- | --- | --- | --- | --- |
|  | C % | H % | N % | Cl % |
| calculated | 50.98 | 6.42 | 9.91 | 12.54 |
| found | 51.12 | 6.20 | 9.80 | 12.63 |

EXAMPLE 4

4-(2-Cycloheptyl-3,3,3-trifluoropropan-1-yl)-imidazole

The desired product is obtained by proceeding as in Example 1 but replacing the cyclopentyl bromide in Step A with cycloheptyl bromide.

Melting point: 185°–190° C.

|  | Elemental microanalysis: | | | |
| --- | --- | --- | --- | --- |
|  | C % | H % | N % | Cl % |
| calculated | 52.62 | 6.79 | 9.44 | 11.95 |
| found | 52.66 | 6.83 | 9.25 | 11.93 |

PHARMACOLOGICAL STUDY OF THE COMPOUNDS OF THE INVENTION

EXAMPLE 5

In vitro affinity test for $\alpha_2$- and $\alpha_1$-receptors

The in vitro affinity tests for $\alpha_2$- and $\alpha_1$-receptors were carried out according to conventional binding methods. The membrane preparations used are rat central nervous system microsomes.

The results of these studies show, for example, that the compound of Example 2 has a $K_{0.5}$ of the order of $5 \times 10^{-8}$ (mol/liter, n=1) in relation to the $\alpha_2$-receptors, and of greater than $10^{-4}$ in relation to the $\alpha_1$-receptors.

As the ratio of $K_{0.5}(\alpha_2)/K_{0.5}(\alpha_1)$ is greater than $10^4$, the affinity of the compounds of the invention in relation to the $\alpha_2$-receptors is supplemented by a high selectivity.

EXAMPLE 6

In vivo $\alpha_2$-antagonism test

The $\alpha_2$-antagonist properties of the compounds of the invention were determined according to a method described by F. Colpaert et al., (DRUG Development Research 7, 125-140, 1986) by measuring the effects produced by those compounds on the loss of the correcting reflex and exophthalmia induced in rats by xylazine, a known agonist of $\alpha_2$-adrenergic receptors in the central nervous system.

The reestablishment of the righting reflex measures the $\alpha_2$-antagonist potential of the compounds, whilst the return of the eye to a normal position measures the $\alpha_1$-antagonist potential.

In this test, the compound of Example 2 has an $ED_{50}$ ($\alpha_2$) of 5 mg/kg and an $ED_{50}$($\alpha_1$) higher than 10 mg/kg, which confirms its selective $\alpha_2$-antagonist properties.

PHARMACEUTICAL COMPOSITION

EXAMPLE 7

Tablet: formulation for the preparation of 1000 2 mg tablets

| | |
|---|---|
| 4-(2-cyclopentyl-3,3,3-trifluoropropan-1-yl)-imidazole | 2 g |
| hydroxypropylcellulose | 2 g |
| cornstarch | 10 g |
| lactose | 100 g |
| magnesium stearate | 3 g |
| talc | 3 g |

We claim:

1. A compound selected from those of formula (I):

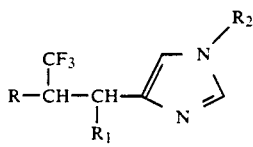

in which

R represents straight-chain or branched lower ($C_1$–$C_6$) alkyl; ($C_3$–$C_8$) cycloalkyl; phenyl unsubstituted or substituted by one or more halogen atoms by one or more straight-chain or branched ($C_1$–$C_6$) alkyl which alkyl groups are themselves unsubstituted or substituted by one or more halogen atoms or by one or more straight-chain or branched ($C_1$–$C_6$) alkoxyl; pyridyl; or naphthyl; and $R_1$ and $R_2$, which are the same or different, each represents hydrogen, straight-chain or branched ($C_1$–$C_6$) alkyl, or straight-chain or branched ($C_1$–$C_6$) acyl, an enantiomer, diastereoisomer, and epimer, thereof and an addition salt thereof with a pharmaceutically-acceptable acid.

2. A compound according to claim 1 in which R represents ($C_3$–$C_8$) cycloalkyl.

3. A compound according to claim 1 in which $R_1$ and $R_2$ simultaneously represent hydrogen.

4. A compound according to claim 1 which is selected from 4-(2-cyclopentyl-3,3,3-trifluoropropan-1-yl)-imidazole, an enantiomer thereof, and an addition salt thereof with a pharmaceutically-acceptable acid.

5. A compound according to claim 1 which is selected from 4-(2-phenyl-3,3,3-trifluoropropan-1-yl)imidazole, an enantiomer thereof, and an addition salt thereof with a pharmaceutically-acceptable acid.

6. A pharmaceutical composition comprising as active ingredient an effective $\alpha_2$-receptor antagonistic amount of compound according to claim 1, in combination with one or more pharmaceutically-acceptable excipients or carriers.

7. A method for treating a living animal afflicted with a condition requiring an antagonist to $\alpha_2$-receptors comprising the step of administering to the said living animal an amount of a compound according to claim 1 which is effective for alleviation of the said condition.

8. A compound according to claim 1 which is selected from 4-(2-cyclohexyl-3,3,3-trifluoropropan-1-yl)-imidazole, an anantiomer thereof, and an addition salt thereof with a pharmaceutically-acceptable acid.

9. A compound according to claim 1 which is selected from 4-(2-cycloheptyl-3,3,3-trifluoropropan-1-yl)-imidazole, an enantiomer thereof, and an addition salt thereof with a pharmaceutically-acceptable acid.

* * * * *

UNITED STATES PATENT AND TRADEMARK OFFICE
CERTIFICATE OF CORRECTION

PATENT NO. : 5,173,502

DATED : Dec. 22, 1992

INVENTOR(S) : Charles Malen, Guillaume de Nanteuil

It is certified that error appears in the above-identified patent and that said Letters Patent is hereby corrected as shown below:

```
Title Page [54], third line; "ANAGONISTS" should read
   -- ANTAGONISTS -- .
Column 1, line 4; "ANAGONISTS" should read -- ANTAGONISTS --.

Column 7, approximately line 37; "atoms" should read -- atoms,--.

Column 8, line 24; "of compound" should read -- of a compound --.

Column 8, line 34; "anantiomer" should read -- enantiomer --.
```

Signed and Sealed this

Thirtieth Day of November, 1993

Attest:

BRUCE LEHMAN

*Attesting Officer*     *Commissioner of Patents and Trademarks*